United States Patent
Cray et al.

(10) Patent No.: US 12,424,331 B2
(45) Date of Patent: Sep. 23, 2025

(54) SYSTEMS AND METHODS FOR MANAGING HEALTH TREATMENT

(71) Applicant: Mental Health Technologies, Inc., Aurora, IL (US)

(72) Inventors: John Cray, Naperville, IL (US); Ernesto Wallerstein, Jr., North Aurora, IL (US)

(73) Assignee: Mental Health Technologies, Aurora, IL (US)

( * ) Notice: Subject to any disclaimer, the term of this patent is extended or adjusted under 35 U.S.C. 154(b) by 61 days.

(21) Appl. No.: 18/532,728

(22) Filed: Dec. 7, 2023

(65) Prior Publication Data

US 2024/0105343 A1    Mar. 28, 2024

(51) Int. Cl.
| | |
|---|---|
| *G16H 50/30* | (2018.01) |
| *G06N 3/02* | (2006.01) |
| *G16H 10/20* | (2018.01) |
| *G16H 10/60* | (2018.01) |
| *G16H 40/20* | (2018.01) |
| *G16H 50/70* | (2018.01) |

(52) U.S. Cl.
CPC .............. *G16H 50/30* (2018.01); *G06N 3/02* (2013.01); *G16H 10/20* (2018.01); *G16H 10/60* (2018.01); *G16H 40/20* (2018.01); *G16H 50/70* (2018.01)

(58) Field of Classification Search
CPC ........ G16H 50/30; G16H 10/20; G16H 10/60; G16H 40/20; G16H 50/70; G16H 10/40; G16H 50/20; G06N 3/02; G06N 5/01; G06N 20/20
See application file for complete search history.

(56) References Cited

U.S. PATENT DOCUMENTS

| | | | |
|---|---|---|---|
| 9,728,101 B2 | 8/2017 | Osborn | |
| 11,568,979 B1 | 1/2023 | Granato | |
| 11,894,146 B2 | 2/2024 | Cray | |
| 2006/0241972 A1 | 10/2006 | Lang | |
| 2010/0249531 A1 | 9/2010 | Hanlon et al. | |
| 2015/0356250 A1 | 12/2015 | Polimeni | |
| 2017/0314081 A1* | 11/2017 | Gutin | .................. C12Q 1/6886 |
| 2019/0026438 A1 | 1/2019 | Ma et al. | |
| 2019/0043623 A1 | 2/2019 | Walington, IV | |

(Continued)

OTHER PUBLICATIONS

United States Patent and Trademark Office, Non-Final Rejection issued in U.S. Appl. No. 18/497,071, dated Jun. 12, 2024 (21 pages).

(Continued)

*Primary Examiner* — Meredith A Long
(74) *Attorney, Agent, or Firm* — Benjamen E. Kern; Risto Pribisich; Kern Kendrick, LLC (57) ABSTRACT

A system and method for managing healthcare diagnosis and treatment may comprise interfaces configured to communicate with internal and external data sources, a workflow engine configured to execute rules on the data, and a machine learning engine configured to process the data and provide the workflow engine with a probability of a test condition. The system and method for managing healthcare diagnosis and treatment may determine, order, send, and execute an appropriate test for a patient. The system and method for managing healthcare diagnosis and treatment may process, record, and communicate the test results.

20 Claims, 8 Drawing Sheets

(56) References Cited

U.S. PATENT DOCUMENTS

| | | |
|---|---|---|
| 2019/0083021 A1 | 3/2019 | Hamilton |
| 2019/0392466 A1 | 12/2019 | Chamberlain et al. |
| 2020/0051679 A1* | 2/2020 | Bostic .................... G16H 10/60 |
| 2020/0090812 A1 | 3/2020 | Condie et al. |
| 2020/0118458 A1 | 4/2020 | Shriberg et al. |
| 2020/0152320 A1 | 5/2020 | Ghazaleh |
| 2021/0241137 A1 | 8/2021 | Jain et al. |
| 2021/0342545 A1 | 11/2021 | Avshalomov |
| 2022/0223399 A1 | 7/2022 | Kaushal et al. |
| 2022/0319705 A1 | 10/2022 | Feuerstein |
| 2023/0010216 A1* | 1/2023 | Lee ........................ G06Q 10/10 |
| 2023/0042882 A1 | 2/2023 | Griffin |
| 2024/0355471 A1* | 10/2024 | Charlap ................ G16H 40/67 |
| 2025/0079011 A1* | 3/2025 | Singh .................... G16H 10/40 |

OTHER PUBLICATIONS

International Search Report and Written Opinion issued on Feb. 18, 2015 in PCT/US2024/059081.

Office Action issued in U.S. Appl. No. 17/383,819, mailing date Jul. 6, 2023.

* cited by examiner

SYSTEMS AND METHODS FOR MANAGING HEALTH TREATMENT

CROSS-REFERENCE TO RELATED APPLICATIONS

Background

In the field of healthcare, diagnostic testing may be a critical component of diagnosis and treatment. Assessing physical disorders may often involve physical testing (e.g., blood tests, imaging, etc.). Assessing mental health (which may also be referred to herein as "behavioral health") may involve the use of standardized, question-based testing for specific conditions, such as anxiety, depression, obsessive compulsive disorder, bipolar disorder, substance abuse, suicide risk severity, and many others.

Assessments may be administered to patients on a periodic basis (e.g., annual check-up), as part of a clinical treatment program to determine condition severity levels during admission, and/or on a regular basis to show progress over time. Providers may use different approaches to testing, which may vary by healthcare organization, by clinic or location, or even by individual provider within a clinic. Often, choices on how to test, when to test, and how often to test may involve a judgment call using patient data that may be incomplete or not optimally organized to make informed decisions.

Mental health testing may be applied to any age group that may be found to be particularly useful in assessing adolescent and pre-adolescent individuals for ADHD, depression, and other conditions. These tests may sometimes be taken or brokered by an intermediary, such as a parent, a guardian, or a teacher. Additionally, since these tests may be standardized and recognized by various health organizations and may be covered as a reimbursable component of treatment by most insurers, assessments may be used by any group wishing to measure a status of the individuals within a community, including clinics, schools, corporate wellness programs, government divisions, and so on. Nevertheless, the traditional mental health treatment methods may be time consuming and slow to manifest the results to legitimize efficacy, limiting insights to model or to focus study on factors to optimize resources to treatment regimen for efficacy progress.

Many healthcare conditions may continue to be undiagnosed until a patient is symptomatic, often until the patient is suffering and must ask for help. Any approach that enables earlier diagnosis of a condition, based on determining a greater-than-normal probability of occurrence, may enable significantly more proactive treatment. This may be particularly true for conditions that are difficult to diagnose through physical testing, such as mental health conditions. But it may also be true when one condition makes another more likely (i.e., comorbidity), or when a combination of factors (e.g., patient demographics, other diagnoses, previous test results in another area, etc.) increase the probability of occurrence, or the worsening, of a particular condition, now or in the future.

Furthermore, if the probability of occurrence of a condition is higher, but testing is negative, providers may not have a clear understanding of how often to retest the patient. Depression and/or suicidality, for example, may be overlooked in primary care because the provider may be guided by state-regulated frequency of minimal testing (e.g., asking two questions once per year) and/or by a lack of understanding of other factors that make these conditions more likely to occur (e.g., life changes, other health issues, etc.)

Yet even if a healthcare facility (e.g., clinic, hospital, etc.) has a good understanding of patient testing regimens, the facility may have insufficient resources to dedicate the effort required to ensure consistency of application of these regimens across its provider and patient population. This may be particularly true when decisions on when and how to test each patient require consideration of multiple factors, including demographic information, family history, past test results, past diagnoses, appointment history, and other data. Any system that could consider all relevant factors, automate the execution of appropriate testing, and utilize results to continue to improve the testing process may remove significant burden from staff and contribute to earlier and more accurate patient diagnostics.

Artificial Intelligence ("AI") may provide a solution for processing large volumes of data for supporting decisions based on that data. However, AI alone may not be capable of properly understanding the context of the data and/or the consequences of decisions based on that data. Therefore, what is needed is a solution that determines and assists in executing healthcare testing by leveraging repeatable logic-based decision making, of the use of AI when appropriate, and the automated ordering of tests to consistently inform the treatment of patients by healthcare professionals.

SUMMARY

In one embodiment, a system for managing healthcare diagnosis and treatment may comprise at least one workflow engine comprising a logic-based engine and configured to allow a user to create at least one triggerable workflow, wherein the workflow may comprise at least one user-defined rule. The system for managing healthcare diagnosis and treatment may further comprise at least one interface configured to communicate with at least one of: a patient, a provider, an EHR/EMR system, an external application, an external data source, and a machine learning engine. The system for managing healthcare diagnosis and treatment may further comprise at least one machine learning engine configured to: a) process an input comprising at least one of a data source, a variable, and a rule, and to b) recognize patterns among the input and generate an output comprising an assignment of a probability relative to the input. The system for managing healthcare diagnosis and treatment may be configured to: a) at least one of recommend, order, and execute an appropriate test based on the output of the machine learning engine; b) administer the appropriate test to a patient; c) process the results of the test; and d) transmit the results of the test.

In one embodiment, a method for managing healthcare diagnosis and treatment may comprise monitoring at least one data source for a workflow trigger comprising at least one of an order, a test result, an appointment, a patient demographic, a patient status, a patient history, a patient communication, and a condition. The method for managing healthcare diagnosis and treatment may further comprise triggering a workflow upon the detection of a workflow trigger, wherein the workflow may comprise: a) a first decision-making layer configured to manage at least one of a rule, a patient test, and a patient communication; b) a second decision-making layer configured to manage at least one workflow, wherein the workflow may comprise at least one rule; and c) a third decision-making layer configured to manage at least one machine learning model. The machine learning model may be configured to process the data relevant to the workflow and to determine a probability of a condition to be tested. The three decision-making layers may be configured to communicate among one another and with external resources. The method for managing healthcare diagnosis and treatment may further comprise executing the steps of the workflow to analyze the data relating to a patient and to determine an appropriate test for the patient. The appropriateness of the test may be determined with the assistance of the machine learning model. The method for managing healthcare diagnosis and treatment may further comprise ordering the test for the patient, and/or administering the test to the patient, processing the results of the test, and transmitting the results of the test.

In one embodiment, a method for managing healthcare diagnosis and treatment may comprise creating on a workflow engine at least one triggerable workflow comprising at least one rule and communicating bi-directionally through an interface with at least one of: a patient, a provider, an EHR/EMR system, an external application, an external data source, and a machine learning engine. The method for managing healthcare diagnosis and treatment may further comprise performing with the machine learning engine: a) processing an input comprising at least one of a data source, a variable, and a rule; b) recognizing patterns among the input; and c) generating an output comprising an assignment of a probability relative to the input. The method for managing healthcare diagnosis and treatment may further comprise determining an appropriate test based on the output of the machine learning engine, ordering the test, and/or administering the test to the patient, processing the test results, and transmitting the test results.

BRIEF DESCRIPTION OF THE DRAWINGS

The accompanying figures, which are incorporated in and constitute a part of the specification, illustrate various example aspects, and are used merely to illustrate various example aspects. In the figures, like elements bear like reference numerals.

DETAILED DESCRIPTION

Embodiments of a Patient Health Testing Engine ("PHTE") system, as described herein, may comprise various aspects to improve at least one of: the content, the effectiveness, and the currency of healthcare testing for patients. The term "healthcare," as used herein, may refer to healthcare broadly and cover all areas of healthcare. Likewise, "healthcare" may refer to one or more focused areas of healthcare, such as without limitation, mental health, dental care, reproductive care, physical therapy, and the like. As such, the PHTE system may be suited for use in any area of healthcare. The improvements of the PHTE system may be based on the execution of a logic-based workflow engine comprising at least one of: a patient's personal data, demographics, and past testing, as well as correlations derived from the analysis of test results from analogous patients in a population.

Figure 1:
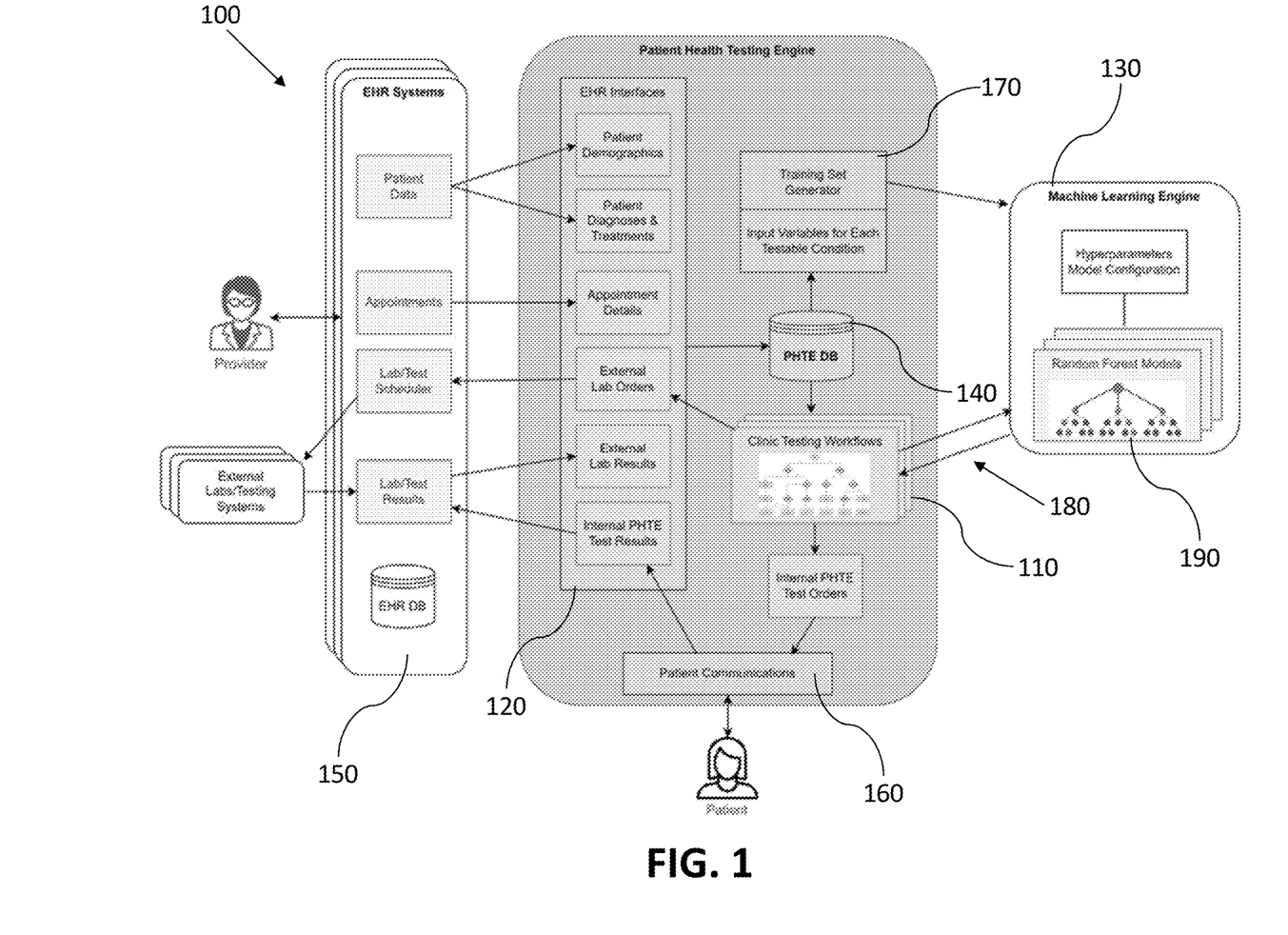
FIG. 1 depicts an example of a system for managing healthcare diagnosis and treatment 100.

FIG. 1 may depict an example of a PHTE system 100, which may enable at least one healthcare practice and its provider(s) to be guided by an expert system to determine when and how to test a patient for a wide range of disorders, and to automatically execute or order these tests based on defined rules. The PHTE system 100 may comprise at least one of: (a) a programmable workflow tool 110 that may be configured to allow the healthcare practice to set up at least one rule that defines which data elements to consider, which tests may be offered based on the possibility or likelihood of a condition, and how tests should be administered to the patient; (b) at least one interface 120 that may be configured to receive the input data on at least one of: a patient, a diagnosis, a treatment, a lab result, an appointment, and the like, and transmit orders and/or test results to a practice's electronic health records ("EHR") or electronic medical records ("EMR") system; and (c) a well-defined interface to, and a training model for, a machine learning engine 130 that may comprise the past results of patient testing across a large population, coupled with other patient data, and may be configured to recognize patterns and assign probabilities to positive tests based upon configurable combinations of these factors.

The PHTE system 100 may recommend, execute, or automatically order tests for the patient. The order and/or the results may be reviewed and/or approved by a provider. The results in turn may be fed back into a PHTE database 140 to gather a greater set of data points over time, which may in turn increase the accuracy of the "learned" correlations and probabilities.

The PHTE system 100 may comprise at least one of the following components:

(1) At least one EHR interface 120, which may comprise two layers: (a) a first layer comprising at least one of a REST API and/or an HL7 interface, which may enable data to be exchanged bi-directionally with an EHR system and/or an EMR system (collectively as EHR systems 150) using secure (e.g., encrypted) communications; and (b) a second layer comprising a set of data mapping models (not shown), which may translate the data from the EHR systems 150 into consistently formatted data for the PHTE database 140, and may enable PHTE test orders and results to be formatted and sent to the EHR systems 150 so that these systems may interpret them and offer them to providers for review and approval.

The PHTE system 100 may support concurrent integration to any number of EHR systems 150 across any number of healthcare organizations. The EHR interfaces 120 may scale horizontally in the architecture of the PHTE system 100 to support such integrations.

The EHR interfaces 120 may operate in real-time and may receive information on at least one of: an updated patient record, an appointment, and a lab result, as they are created or modified in the EHR systems 150. The EHR interfaces 120 may also send new lab orders and/or test results to the EHR systems 150 as they are generated by the PHTE system 100.

(2) At least one clinic testing workflow engine 110, which may comprise a logic-based engine that may enable the definition and the execution of a set of triggerable workflows that may be configured uniquely for each healthcare facility/clinic.

The clinic testing workflow engine 110 may include a visual workflow creation tool (not shown) that may enable the definition of at least one rule governing when and/or how at least one patient may be tested, as well as a run-time environment (not shown) where any number of workflow instances may be run either sequentially or concurrently. The run-time environment may scale horizontally to support larger numbers of concurrent workflows and their tasks.

Each clinic/facility may have its own unique set of workflows. Each workflow may be triggered by a specific trigger type, including triggers for at least one of: a new patient, a modified patient, a new appointment, a modified appointment, a cancelled appointment, and the like. When triggered, a workflow may execute a series of tasks, which may include at least one of: conditional testing and branching, creation of data records, inclusion of test types, scheduling or running PHTE internal tests based on time-based rules, and scheduling or ordering external tests based on time-based rules.

Each instance of a workflow may be specific to a particular patient and/or to a particular triggering event (e.g., an appointment). The workflow instance may have access to some, or all, of the data elements associated with that trigger and/or stored within the PHTE system 100, including at least one of: a patient demographic, a patient diagnosis, a patient treatment, an appointment data (e.g., provider, reason, etc.), and a past lab and/or test result (e.g., time, scoring, and other data). Each of these elements may be used in conditional logic to determine when and/or how to test the patient.

If enabled, the workflow may also use the output of a machine learning engine 130, which may take a set of input parameters and return a probability of positive occurrence of a testable condition. The machine learning engine 130 may be used one or more times from the workflow for different testable conditions, and the probabilities returned may also be used in conditional logic to determine whether to order one or more of an external test or a PHTE internal test (e.g., if the probability is greater than 20% for anemia, order an appropriate blood test).

(3) At least one patient communications interface 160 (e.g., for internal PHTE testing), which may comprise a set of communications interfaces that may allow the PHTE testing to be done directly with the patients of a healthcare facility without the need for an interface to external labs/testing systems (e.g., via an EHR/EMR).

The patient communications interface 160 may allow the PHTE-generated tests, which may be in the form of a rules-driven question and answer survey, to be sent to patients via several different communications methods, including a text/SMS, an email, a physical device, and the like. The methods used for patient communication may be defined at a healthcare facility/clinic level and may be further defined/refined within the workflows executed by the clinic testing workflow engine 110.

When a patient receives a communication (which may include one or more tests), the patient may interact with at least one input/output form that may be designed to fit the patient's input device. The answers may be communicated to the PHTE system 100 in real-time so that the PHTE system 100 may retain context at an individual question level. If a patient suspends the interaction and returns later, the forms may pick up the interaction where the patient previously left off.

The test answers may be compiled by the PHTE system 100, interpreted based on rules specific to each type of test, and stored in the PHTE database 140. The scores, interpretations, and details may also be communicated to the clinic's EHR System 150 instance via the EHR interfaces 120. The EHR System 150 may provide a workflow, which may allow at least one provider to view, approve, and/or associate the results with the patient's chart and visit.

(4) At least one machine learning engine 130, which may support testing decisions based on the probability of a particular condition. The PHTE system 100 may support at least one external interface to the machine learning engine 130. The machine learning engine 130 may test decisions when an instance of a workflow executed by the clinic testing workflow engine 110 makes a request to the machine learning engine 130. The request may include a specific set of input parameters and a desired condition variable (e.g., configured for that particular type of request). When the machine learning engine 130 returns its response (e.g., in the form of the probability of the specified condition), the workflow may then use this to guide patient testing decisions.

The PHTE system 100 may include two different interfaces to the machine learning engine 130: a) a training set generator 170, which may generate datasets used to train the machine learning engine 130; and b) a transactional interface 180, which may allow the clinic testing workflow engine 110 to make requests to the machine learning engine 130 for individual condition probabilities while executing a workflow.

The machine learning engine 130 may support at least one machine learning model, which may be trained with a supervised learning method, an unsupervised learning method, and/or combinations of each. Various machine learning model types have the strengths and weaknesses depending upon the circumstances of their use. As such, the machine learning engine 130 may comprise any type of machine learning model.

The machine learning model may be selected based on several criteria, such as at least one of: an accuracy, a robustness, a flexibility, a speed, and a transparency. For example, the machine learning model may comprise at least one random decision forest 190. Regarding accuracy, the random decision forest 190 may have a high degree of accuracy relative to other model types when trained with a large dataset.

Regarding robustness, the random decision forest 190 may support a higher number of input parameters than many other model types. Furthermore, the random decision forest 190 may not be subject to geometric complexity growth with higher dimensionality (as with a more basic single decision tree model).

Regarding flexibility, the random decision forest 190 may support both continuous input variables (e.g., a degree of a condition, such as the value of a test) and categorical input variables (e.g., one of a set of value types, such as gender or ethnicity). Furthermore, the random decision forest 190 may work well with missing data, such as when the input parameter set for patients (e.g., in training and/or in transactional usage) may be incomplete. Likewise, the random decision forest 190 may support a higher level of variance in the input data, which may generally be prevalent in larger patient populations.

Regarding speed, the training time for the random decision forest 190 may be higher than other model types, but with respect to the PHTE system 100, the random decision forest 190 may not require rapid training Instead, the training may be performed separately for each output condition variable, and each training run may be done and repeated (e.g., when additional sufficient data is collected) on its own schedule.

Regarding transparency, the output of the random decision forest 190 may have some level of transparency, as contrasted with neural networks and regression models. This transparency may allow for the logging of specific decision paths across multiple trees, which may then be averaged to generate a probability, based on the values of a provided set of input parameters. This transparency may be useful when defending the model's approach and efficacy with a clinic director and/or provider community, as it may be easier to understand "why" the model works for certain conditions.

The PHTE system 100 may allow the configuration of any number of condition variable types (i.e., dependent variables), each with its own defined set of allowed input parameter types (i.e., independent variables). During training (e.g., generation of all decision trees), the PHTE system 100 may enable the generation of a specified number of randomized datasets, each using a subset of data points and a subset of input parameters (i.e., features). This data may be fed to the random decision forest 190 for generation of the forest for each condition variable type. Training for each condition variable may be done separately and may be executed on any specified schedule.

Once the forest is created for a condition variable type, the forest may be used by the clinic testing workflow engine 110 to obtain a condition probability for a specific patient based on the input parameters available for that patient. The PHTE system 100 may use the transactional interface 180 to send these parameters to the machine learning engine 130, and the appropriate step in the workflow for the patient may then be informed with a condition probability that it may utilize to determine the next step. This may typically be whether a test (e.g., external lab or PHTE internal test) is scheduled/ordered.

Figure 2:
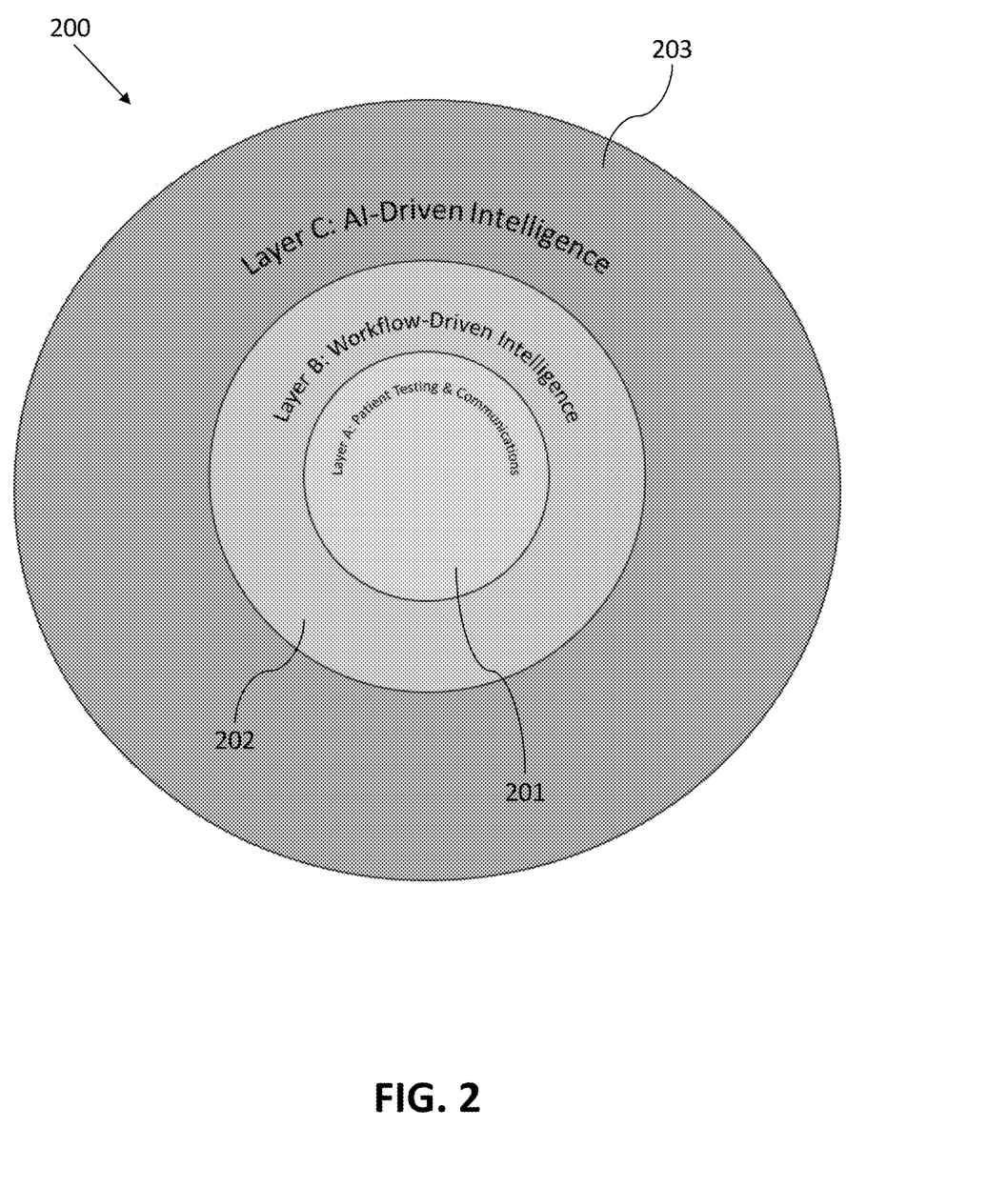
FIG. 2 depicts an example of a layered decision-making capability of a system for managing healthcare diagnosis and treatment 200.

FIG. 2 may depict a layered decision-making capability of a PHTE system 200, which may provide flexibility in the form of a logical "layered" architecture. Each layer (which may also be referred to herein as "sections") may add a greater configurability and a greater intelligence to the decision making of the PHTE system 200 on patient testing.

Referring to FIG. 2, the decision-making layers 200 may comprise the following:
(1) A Layer A 201, which may represent the innermost layer and the core capabilities of the PHTE system 200 for executing a patient PHTE internal testing and the ordering of an external lab test. The PHTE internal tests may comprise: the definitions of a test format, a rule, and a scoring; the ability to schedule and send the tests and receive the results via a patient communication; and the ability to store the test results and make them available to at least one EHR System (not shown). For the external lab orders, this may comprise the ability to communicate an order type and an order schedule to the EHR systems. On its own (i.e., without a Layer B 202 and without a Layer C 203), the Layer A 201 may execute the tests and/or the orders but may only do so upon a demand from a user.
(2) The Layer B 202, which may represent the second, or middle, layer and a clinic testing workflow engine (not shown), which in turn may include the definition of at least one workflow at a clinic level and/or at a trigger level. The Layer B 202 may comprise a trigger handling and/or a trigger logic that may define the execution of each instance of each workflow to determine how and/or when each patient may be tested (i.e., when a trigger event may be invoked). Without the Layer C 203, the Layer A 201 and the Layer B 202 together may use conditional logic to execute the internal PHTE testing and the external lab ordering based on at least one of the following input parameters: a patient's demographics, a previous test and lab results, a diagnosis and a treatment (e.g., current and past), and an appointment's information. The Layer A 201 and the Layer B 202 together may perform some or all of the logic-based decision making and execution for all configured patient tests and labs.
(3) The Layer C 203, which may represent the outermost layer and the ability of the PHTE system 200 to leverage an external machine learning engine (not shown) to supplement the workflow logic in the Layer B 202 with the calculated probabilities of at least one potential patient condition. This may then be used in the logic to contribute to the determination of when and/or how to test a patient. The machine learning engine may comprise at least one machine learning model (not shown), which may be trained by random datasets derived from the PHTE database (not shown), which may contain positive and/or negative cases associated with configured sets of input parameters. The machine learning model may comprise at least one random decision forest (not shown). After training, as each workflow (e.g., from the Layer B 202) is executed, the condition probabilities for the patient associated with that workflow may be available at each appropriate step in the workflow.

Even without the Layer C 203, the PHTE system 200 may contain a significant decision-making capability for determining patient testing and ordering for every trigger event, with highly configurable rules for every clinic and healthcare facility. Optionally, the Layer C 203 may be added to utilize data correlations from a much larger set of data that may span, for example, hundreds of thousands of patients across a large number of healthcare facilities, in a model that maximizes the accuracy of condition probabilities derived from this large dataset.

Figure 3:
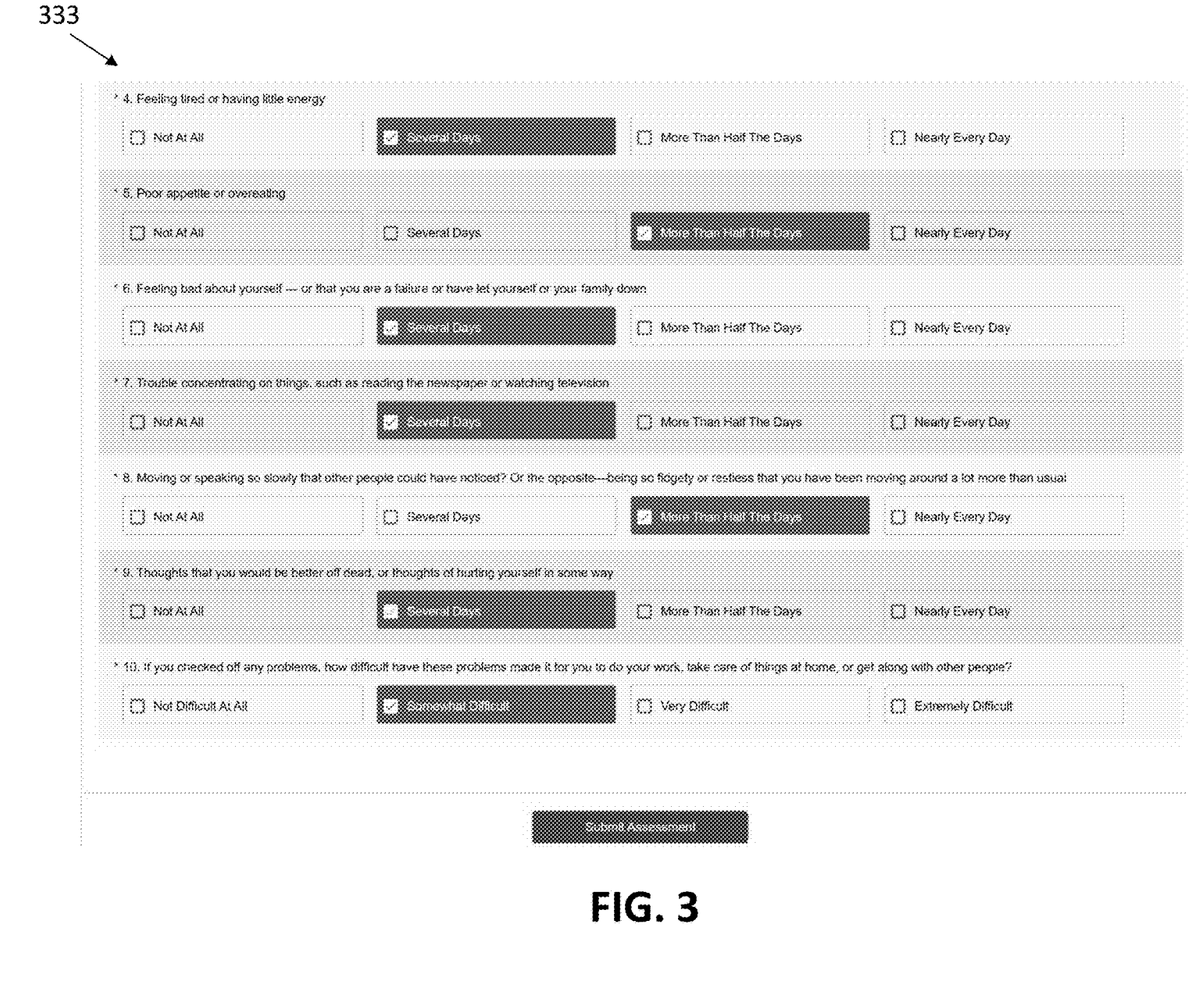
FIG. 3 depicts an example of a patient assessment 333.

FIG. 3 may depict an example of a PHTE internal test 333 completed by a patient and analyzed using a PHTE scoring and interpretation. In this example, the patient may be presented with questions and selectable answers for a depression survey. Once the test 333 is completed and submitted, the PHTE system (not shown) may score the test 333 and interpret the results.

Figure 4:
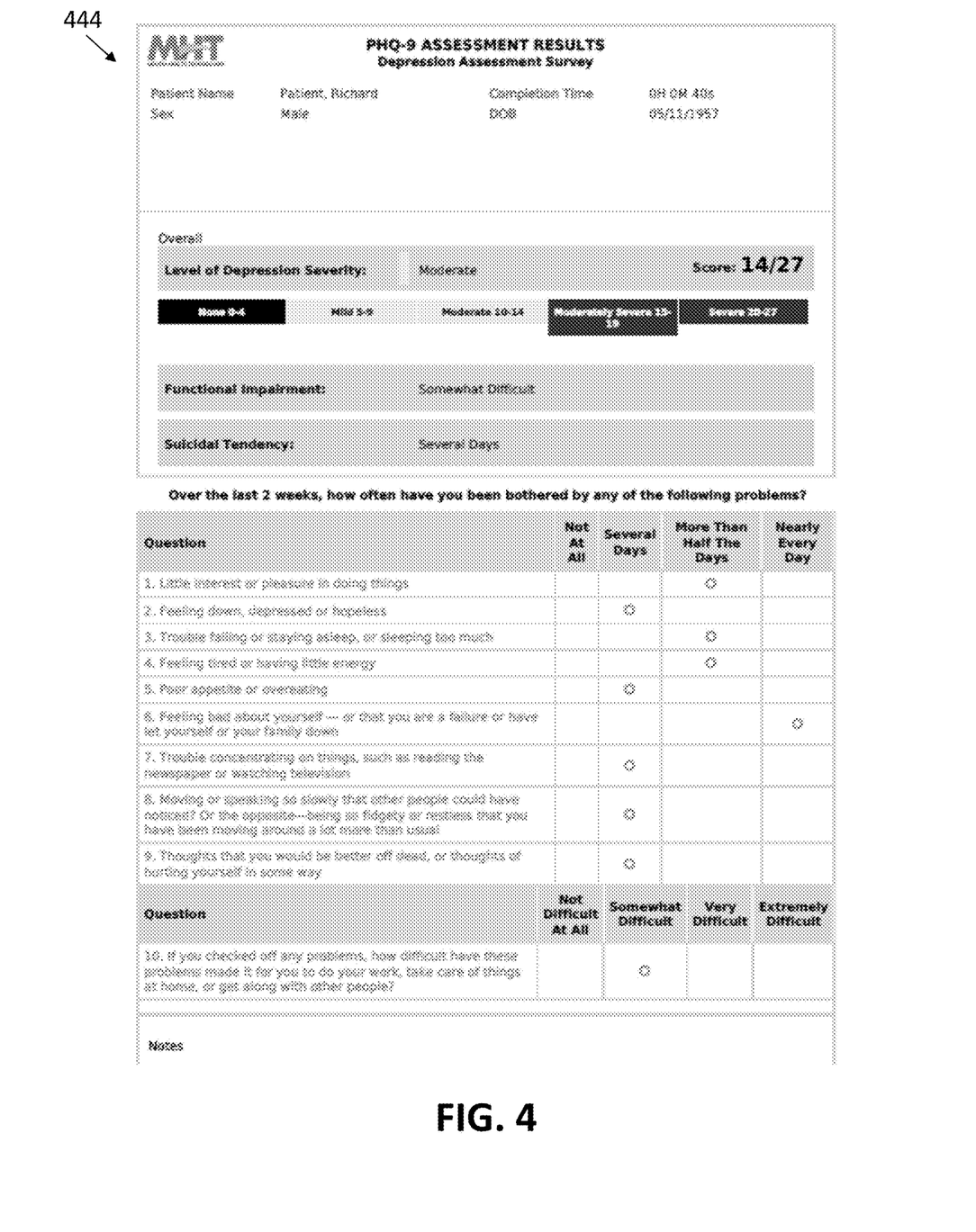
FIG. 4 depicts an example of a patient's test results 444.

FIG. 4 may depict an example of a test result 444 after a test has been completed by a patient and scored and/or interpreted by a PHTE system (not shown).

Figure 5:
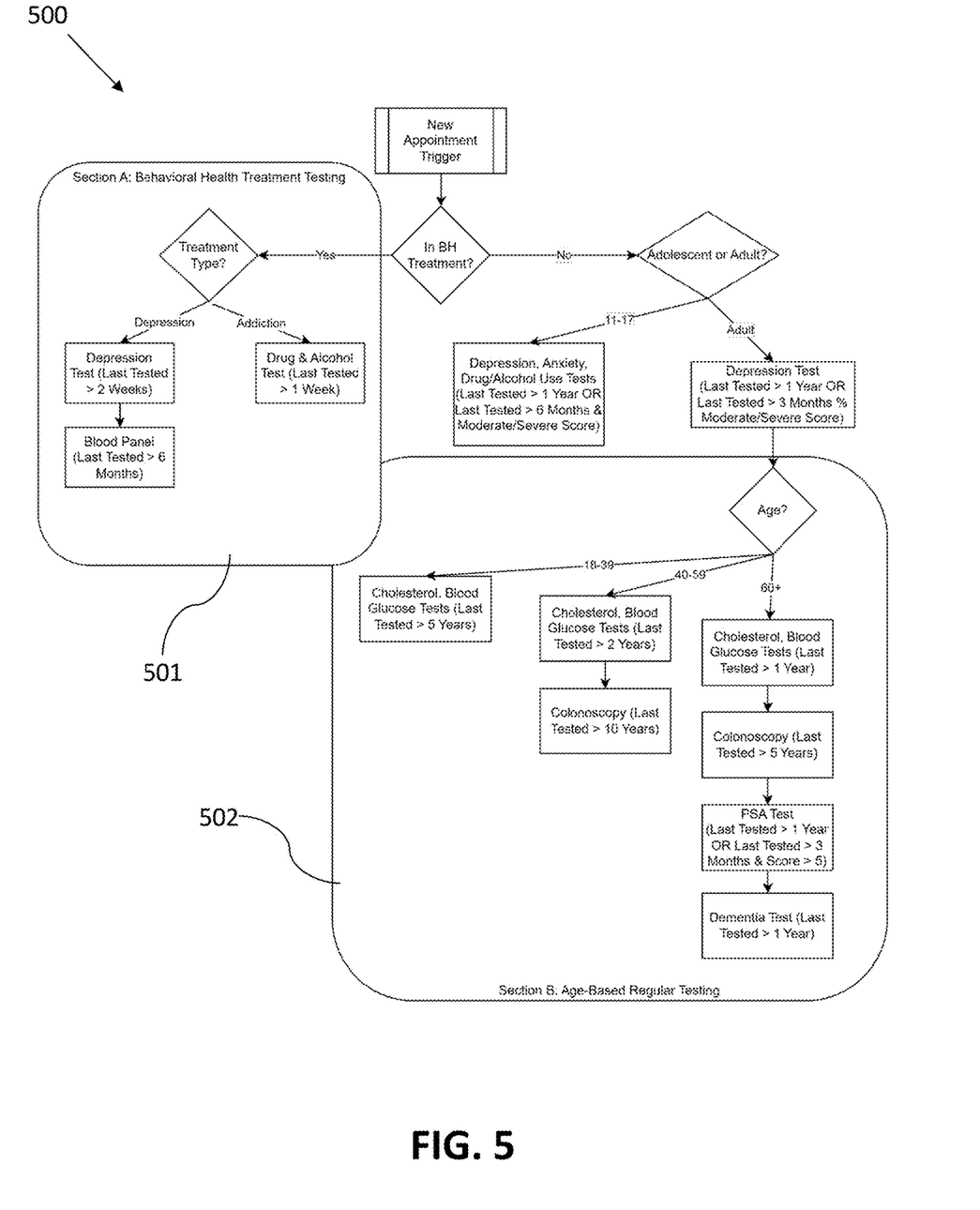
FIG. 5 depicts an example workflow for a system and a method for managing healthcare diagnosis and treatment 500.

FIG. 5 may depict an example workflow of a PHTE system 500, which may be triggerable for new patient appointments. The workflow may comprise a Section A 501 and a Section B 502.

The workflow may make patient testing decisions for several test types based on at least one of: a patient's age, a patient's treatment status, a time since a last test, and a score/interpretation of the last test. The logic supporting the workflow may be dependent upon the data available in the PHTE system 500 and in the patient record in the EHR System (not shown). At least one action may execute both PHTE internal tests and external lab orders. In the workflow, there may be no use of analysis from an external machine learning engine (not shown).

The Section A 501 of the workflow may contain the rules and the execution of tests (and test frequency) for patients in mental health treatment, which may show a more frequent cadence of testing than for patients not in mental health treatment. The Section B 502 of the workflow may show regular testing based on patient age, previous test dates, and the results.

Figure 6:
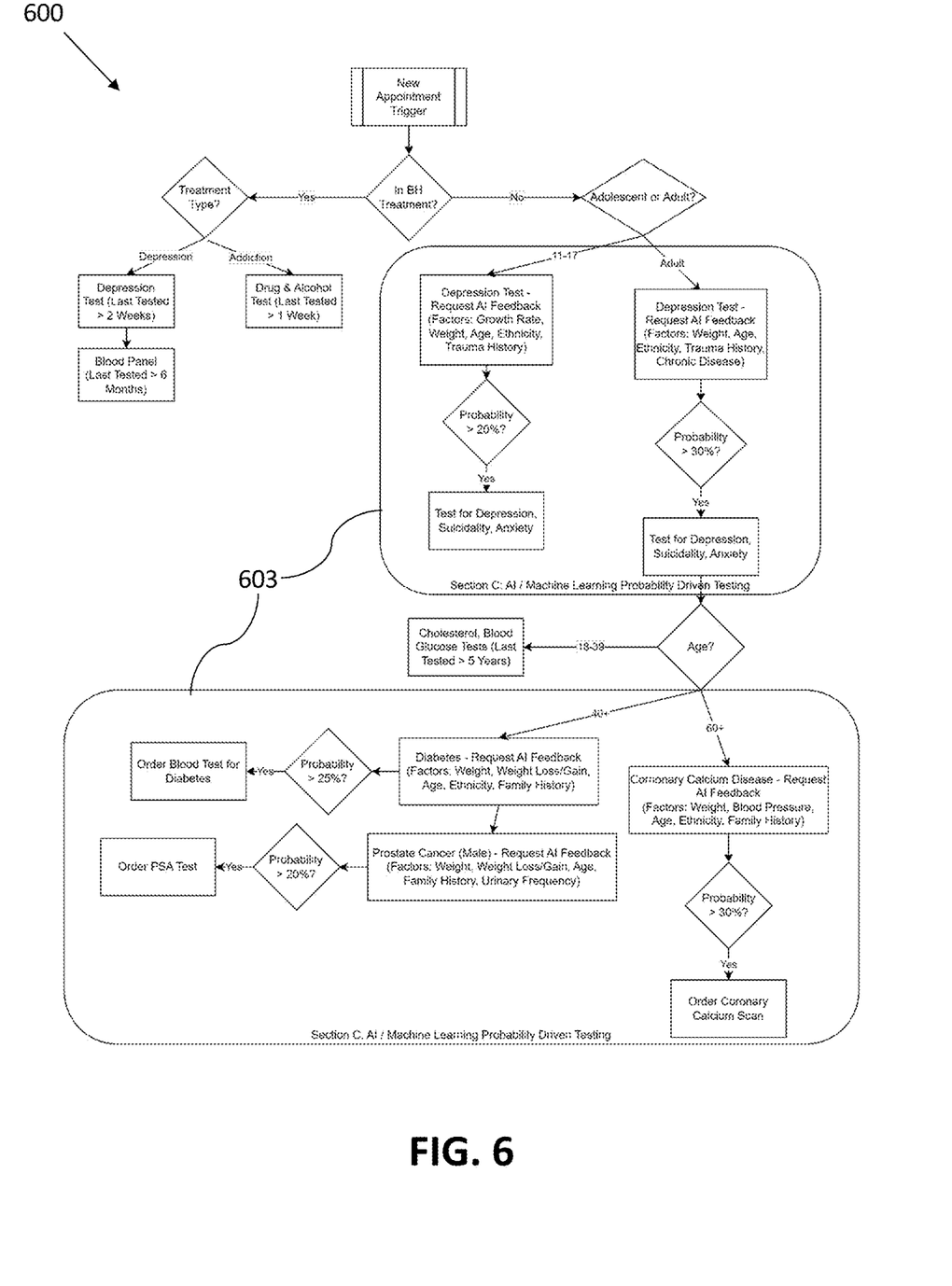
FIG. 6 depicts an example AI-driven workflow for a system and a method for managing healthcare diagnosis and treatment 600.

FIG. 6 may depict an example workflow for a PHTE system 600, which may be triggerable for new patient appointments. The workflow may comprise a Section C 603.

The workflow may make patient testing decisions based on probabilities returned from a machine learning engine (not shown). The Section C 603 of the workflow may comprise blocks that request artificial intelligence ("AI") feedback from at least one machine learning model (not shown) based on input parameters that may differ for each condition type being assessed. The machine learning engine may return a probability, which may then be used in the logic to drive testing decisions for the patient. The workflow may combine these AI probability-driven decisions for testing (shown in the Section C 603) with more standard logic-based decisions, such as those of a Section B (not shown).

Figure 7:
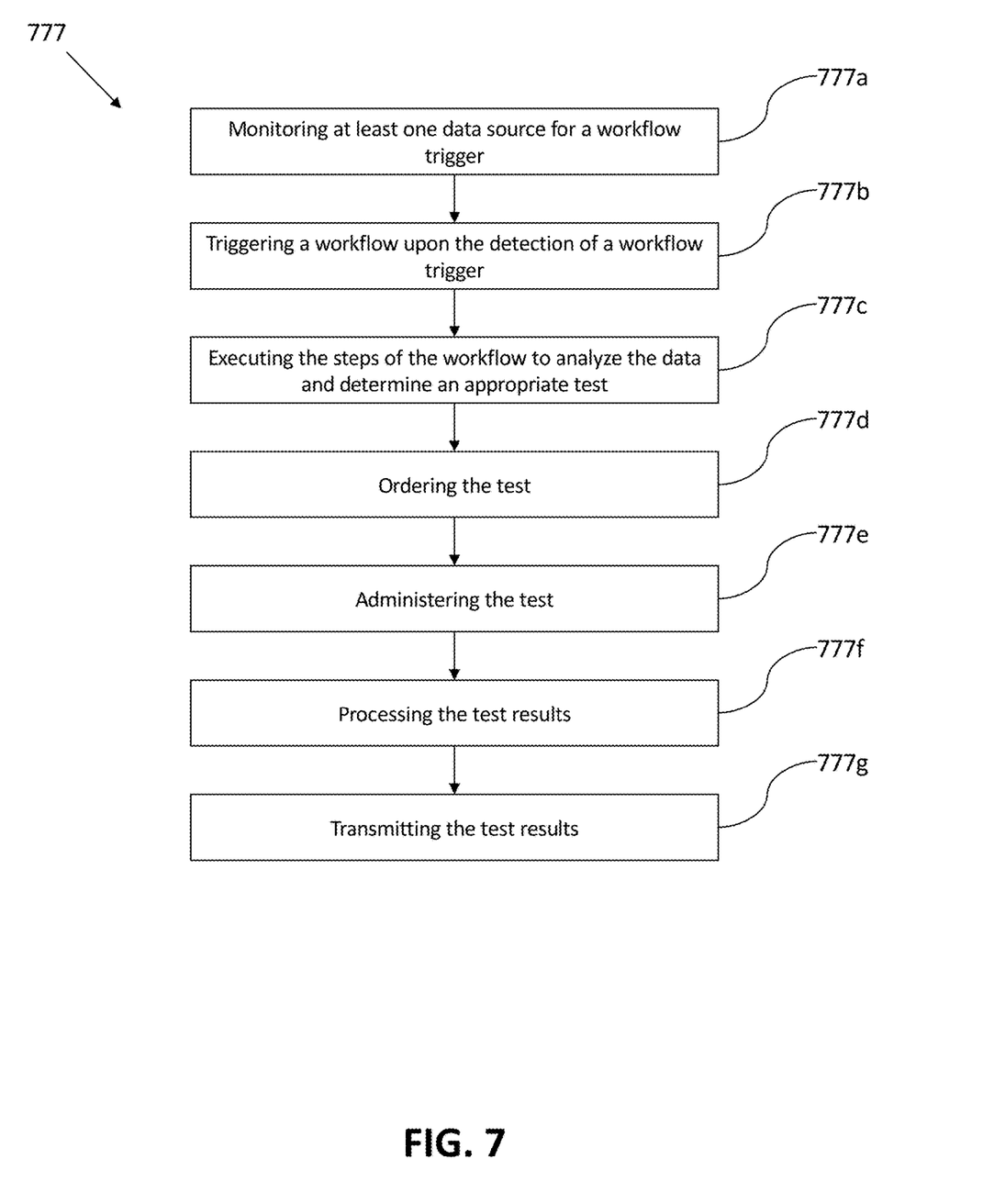
FIG. 7 depicts an example method for managing healthcare diagnosis and treatment 777.

FIG. 7 may depict a method for managing healthcare diagnosis and treatment 777, which may comprise: monitoring at least one data source for a workflow trigger 777a, triggering a workflow upon the detection of a workflow trigger 777b, executing the steps of the workflow to analyze the data relating to a patient and to determine an appropriate test 777c, and/or ordering the test 777d, administering the test 777e, processing the test 777f, and transmitting the test results 777g.

Monitoring at least one data source for a workflow trigger 777a may comprise at least one of an order, a test result, an appointment, a patient demographic, a patient status, a patient history, a patient communication, and a condition. The at least one data source may be an internal data source, such as a PHTE database, or it may be an external data source, such as a patient, a provider, an EHR/EMR system, an external application, an external data source, and a machine learning engine.

A workflow may be triggered upon the detection of a workflow trigger 777b. The workflow may comprise: a first decision-making layer configured to manage at least one of a rule, a patient test, and a patient communication; a second decision-making layer configured to manage at least one workflow; and a third decision-making layer configured to manage at least one machine learning model. The workflow may comprise at least one rule. The machine learning model may be configured to process the data relevant to the workflow and to determine a probability of a condition to be tested. The three decision-making layers may be configured to communicate among one another and with external resources.

The steps of the workflow may be executed to analyze the data relating to a patient and to determine an appropriate test for the patient 777c. The appropriateness of the test may be determined with the assistance of the machine learning model. Once the appropriate test has been determined, the method may comprise ordering the test for the patient 777d, and/or administering the test to the patient 777e, processing the results of the test 777f, and transmitting the results of the test 777g. The results of the test may be transmitted to at least one of: a patient, a provider, an EHR/EMR system, an external application, an external data source, a database, and a machine learning engine.

The method for managing healthcare diagnosis and treatment 777 may be executed by, and/or with the assistance of, at least one computer. The computer may be local or cloud-based and may comprise at least one of: a processor (e.g., a CPU or a GPU, as is well known in the art), a memory, a storage medium, a transitory computer-readable medium, a non-transitory computer-readable medium, a network interface, and a graphic interface. The computer may be configured to execute at least one program instruction to cause the computer processor to execute the method for managing healthcare diagnosis and treatment 777.

The method for managing healthcare diagnosis and treatment 777 may further comprise transmitting the results of the test to at least one of: a patient, a provider, an EHR/EMR system, an external application, an external data source, a database, and a machine learning engine. The results may be transmitted bi-directionally by at least one of a REST API and an HL7 interface.

The method for managing healthcare diagnosis and treatment 777 may further comprise feeding the results of the test back into the workflow engine as an input and processing the test results with the machine learning engine to increase the accuracy of the machine learning engine.

The method for managing healthcare diagnosis and treatment 777 may further comprise generating a training dataset with a training set generator; creating a training model by training a machine learning model with the training dataset; and training the machine learning engine with the training model. At least one of the training model and the machine learning engine may comprise at least one random decision forest.

Figure 8:
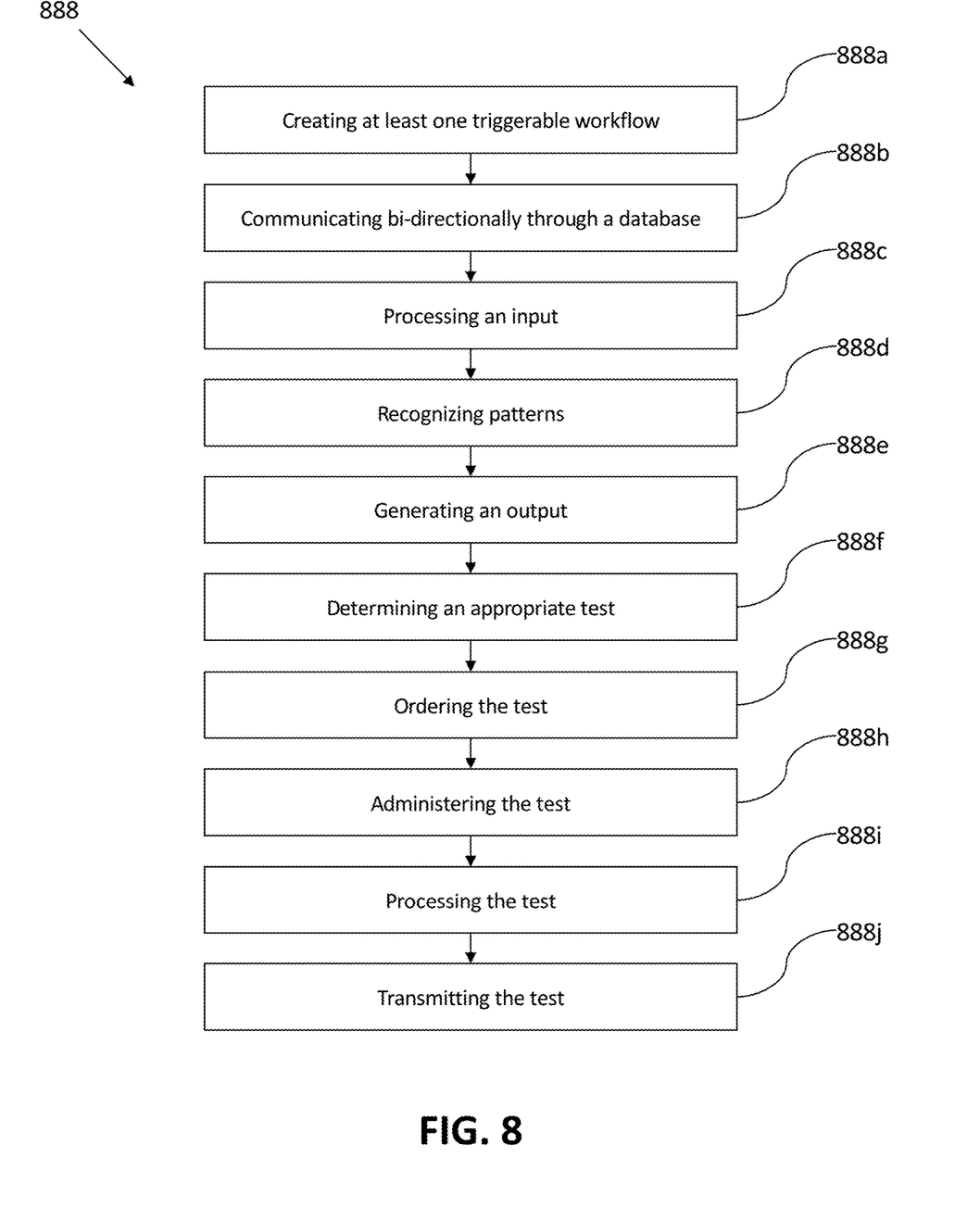
FIG. 8 depicts an example method for managing healthcare diagnosis and treatment 888.

FIG. 8 may depict a method for managing healthcare diagnosis and treatment, which may comprise: creating on a workflow engine at least one triggerable workflow 888a; communicating bi-directionally through an interface 888b; performing with the machine learning engine: a) processing an input 888c, b) recognizing patterns among the input 888d, and c) generating an output 888e; determining an appropriate test based on the output of the machine learning engine 888f; ordering the test 888g; administering the test to the patient 888h; processing the test results 888i; and transmitting the test results 888j.

Regarding creating on a workflow engine at least one triggerable workflow 888a, the triggerable workflow may comprise at least one rule. Regarding communicating bi-directionally through an interface 888b, the bi-directional communication may be with at least one of: a patient, a provider, an EHR/EMR system, an external application, an external data source, and a machine learning engine. Regarding processing an input 888c, the input may comprise at least one of a data source, a variable, and a rule. Regarding generating an output 888e, the output may comprise an assignment of a probability relative to the input.

The method for managing healthcare diagnosis and treatment 888 may further comprise: storing, in a database, at least one of the input, the output, and the test results; and feeding the test results back into the workflow engine as an input and processing the test results with the machine learning engine to increase the accuracy of the machine learning engine.

The method for managing healthcare diagnosis and treatment 888 may further comprise: generating a training dataset with a training set generator; creating a training model by training a machine learning model with the training dataset; and training the machine learning engine with the training model. At least one of the training model and the machine learning engine may comprise at least one random decision forest.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "substantially" is used in the specification or the claims, it is intended to take into consideration the degree of precision available in the relevant art. To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function, whether the designated function is expressly designated herein or well known to a person having ordinary skill in the art. As used in the specification and the claims, the singular forms "a," "an," and "the" include the plural. Finally, where the term "about" is used in conjunction with a number, it is intended to include ±10% of the number. In other words, "about 10" may mean from 9 to 11.

As stated above, while the present application has been illustrated by the description of embodiments and aspects thereof, and while the embodiments and aspects have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

What is claimed is:

1. A method for managing healthcare diagnosis and treatment, comprising:
    monitoring at least one data source for a workflow trigger comprising at least one of an order, a test result, an appointment, a patient demographic, a patient status, a patient history, a patient communication, and a condition;
    triggering a workflow upon the detection of a workflow trigger, wherein the workflow comprises:
        a first decision-making layer configured to manage at least one of a rule, a patient test, and a patient communication;
        a second decision-making layer configured to manage at least one workflow, wherein the workflow comprises at least one rule; and
        a third decision-making layer configured to manage at least one machine learning model, wherein the machine learning model is configured to process data relevant to the workflow and to determine a probability of a condition to be tested;
        wherein the three decision-making layers are configured to communicate among one another and with external resources;
    executing the steps of the workflow to analyze data relating to a patient and to determine an appropriate test for the patient, wherein the appropriateness of the test is determined with the assistance of the machine learning model;
    ordering the test for the patient; and/or
    administering the test to the patient;
    processing the results of the test; and
    transmitting the results of the test.

2. The method for managing healthcare diagnosis and treatment according to claim 1,
    wherein a machine learning engine comprises the machine learning model;
    wherein the results of the test are transmitted to at least one of: a patient, a provider, an electronic health records system, an electronic medical records system, an external application, an external data source, a database, and the machine learning engine; and
    wherein the results are transmitted bi-directionally by at least one of a representational state transfer application program interface and an health level 7 interface.

3. The method for managing healthcare diagnosis and treatment according to claim 1,
    wherein a machine learning engine comprises the machine learning model; and
    the method further comprising feeding the results of the test back into a workflow engine as an input and processing the test results with the machine learning engine, which increases the accuracy of the machine learning engine.

4. The method for managing healthcare diagnosis and treatment according to claim 1, further comprising:
    generating a training dataset with a training set generator;
    creating a training model by training a machine learning model with the training dataset; and
    training a machine learning engine with the training model.

5. The method for managing healthcare diagnosis and treatment according to claim 4, wherein at least one of the training model and the machine learning engine comprise at least one random decision forest.

6. The method of managing diagnosis of treatment according to claims 5, wherein for each of the at least one random decision forest, data is fed into the random decision forest to generate a forest for each condition variable type of the data.

7. The method of managing diagnosis and treatment according to claim 1, further comprising feeding data relating to a patient and the appropriate test for the patient into a workflow engine as inputs and processing the inputs with a machine learning engine to increase the accuracy of the machine learning engine.

8. The method of managing diagnosis and treatment according to claim 1, further comprising storing in a database data pertaining to the at least one of an order, a test result, an appointment, a patient demographic, a patient status, a patient history, a patient communication, and a condition.

9. The method of managing diagnosis and treatment according to claim 8, further comprising feeding data stored in the database pertaining to the at least one of an order, a test result, an appointment, a patient demographic, a patient status, a patient history, a patient communication, and a condition into a workflow engine as an input and processing the input with a machine learning engine to increase the accuracy of the machine learning engine.

10. The method of managing diagnosis and treatment according to claim 1, further comprising processing one or more input;
wherein the step of determining a probability of a condition to be tested includes the machine learning model recognizing patterns among the one or more input.

11. The method of managing diagnosis of treatment according to claim 10, wherein the one or more inputs comprise at least one of a data source, a variable, and a rule.

12. The method of managing diagnosis of treatment according to claim 1, further comprising transmitting the test to the patient.

13. The method of managing diagnosis of treatment according to claim 1, further comprising receiving the results of the test from the patient.

14. A method for managing healthcare diagnosis and treatment, comprising:
creating on a workflow engine at least one triggerable workflow comprising at least one rule;
communicating bi-directionally through an interface with at least one of: a patient, a provider, an electronic health records system, electronic medical records system, an external application, an external data source, and a machine learning engine;
performing with the machine learning engine:
processing an input comprising at least one of a data source, a variable, and a rule;
recognizing at least one pattern among the input; and
generating an output comprising an assignment of a probability relative to the input;
determining an appropriate test based on the output of the machine learning engine;
ordering the test; and/or
administering the test to the patient;
processing the test results; and
transmitting the test results.

15. The method for managing healthcare diagnosis and treatment according to claim 14, further comprising:
storing, in a database, at least one of the input, the output, and the test results; and
feeding the test results back into a workflow engine as an input and processing the test results with a machine learning engine to increase the accuracy of the machine learning engine.

16. The method for managing healthcare diagnosis and treatment according to claim 14, further comprising:
generating a training dataset with a training set generator;
creating a training model by training a machine learning model with the training dataset; and
training a machine learning engine with the training model;
wherein at least one of the training model and the machine learning engine comprises at least one random decision forest.

17. The method of managing diagnosis of treatment according to claims 16, wherein for each of the at least one random decision forest, data is fed into the random decision forest to generate a forest for each condition variable type of the data.

18. The method of managing diagnosis and treatment according to claim 14, further comprising feeding data relating to a patient and the appropriate test for the patient into the workflow engine as inputs and processing the inputs with a machine learning engine to increase the accuracy of the machine learning engine.

19. The method of managing diagnosis of treatment according to claim 14, further comprising transmitting the test to the patient.

20. The method of managing diagnosis of treatment according to claim 14, further comprising receiving the results of the test from the patient.

* * * * *